(12) United States Patent
Klun

(10) Patent No.: US 7,935,306 B2
(45) Date of Patent: May 3, 2011

(54) MEASUREMENT SYSTEM

(75) Inventor: Wolfgang Klun, Inglostadt (DE)

(73) Assignee: Ebro Electronic GmbH & Co. KG, Ingolstadt (DE)

( * ) Notice: Subject to any disclaimer, the term of this patent is extended or adjusted under 35 U.S.C. 154(b) by 1237 days.

(21) Appl. No.: 11/286,892

(22) Filed: Nov. 23, 2005

(65) Prior Publication Data

US 2006/0145840 A1 Jul. 6, 2006

(30) Foreign Application Priority Data

Nov. 24, 2004 (DE) .......................... 10 2004 056 796

(51) Int. Cl.
*G01N 33/00* (2006.01)
(52) U.S. Cl. ................. 422/5; 422/62; 422/83; 422/547
(58) Field of Classification Search ................ 422/5, 62, 422/83, 547
See application file for complete search history.

(56) References Cited

U.S. PATENT DOCUMENTS

| | | | |
|---|---|---|---|
| 3,982,893 | A | 9/1976 | Joslyn |
| 5,426,428 | A | 6/1995 | Binder et al. |
| 5,491,092 | A | 2/1996 | Colvin |
| 6,156,267 | A | 12/2000 | Pai et al. |
| 6,308,574 | B1 | 10/2001 | Klun et al. |
| 6,532,794 | B2 | 3/2003 | Wang et al. |
| 6,536,060 | B1 | 3/2003 | Janssens et al. |
| 2003/0115933 | A1 | 6/2003 | Wang et al. |

FOREIGN PATENT DOCUMENTS

| | | |
|---|---|---|
| DE | 3545215 | 11/1986 |
| DE | 4031981 A1 | 4/1992 |
| DE | 29809662 U1 | 9/1998 |
| DE | 19714880 C2 | 10/1998 |
| DE | 29901030 U1 | 5/1999 |
| EP | 0231431 | 1/1990 |
| EP | 0604387 | 6/1996 |
| EP | 0671956 | 8/2002 |
| WO | WO 9321964 * | 5/1993 |

OTHER PUBLICATIONS

Examination Report issued in counterpart New Zealand Application No. 543718 dated Nov. 29, 2005; 1 page.
Search Report issued in counterpart German Application No. 102004056796.4 dated Sep. 22, 2005; 4 pages.
Search Report issued in counterpart European Application No. 05110736.5 dated Apr. 18, 2006; 3 pages.

* cited by examiner

*Primary Examiner* — Sam P Siefke
(74) *Attorney, Agent, or Firm* — Dority & Manning, P.A.

(57) ABSTRACT

A system and method (1) for acquiring, compiling and storing measured values in a temperature and/or pressure and/or moisture-dependent process comprises at least one sensor (4, 6) for acquiring measured values. The device (1) contains means (3) for storing the measured values. The sensor (4, 6) and the means (3) are designed to be positioned inside a closed process chamber (2). The device (1) further comprises means (11) for the wireless transmission of the stored measured values at preset or settable time intervals to a receiver unit (10) disposed outside the closed process chamber (2). In a process for monitoring a temperature and/or pressure and/or moisture-dependent process, an acquisition of measured values is accomplished by means of at least one sensor (4, 6) located inside a closed process chamber (2). The acquired measured values are compiled and stored in at least one data logger (3), and during the process are transmitted at preset or settable time intervals to a receiver unit (10) located outside the process chamber (2), by means of a wireless system.

17 Claims, 1 Drawing Sheet

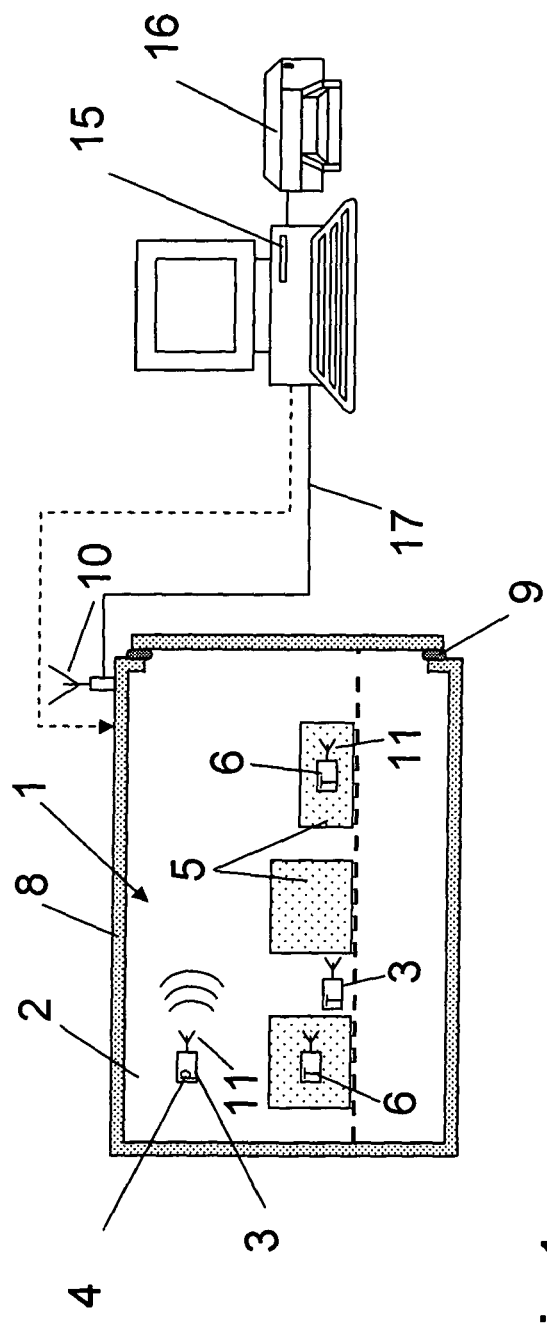
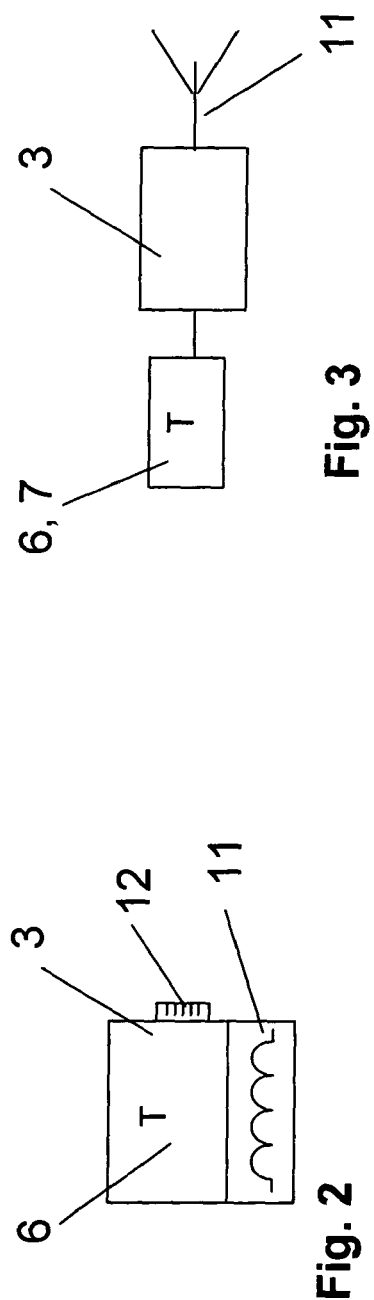

MEASUREMENT SYSTEM

REFERENCE TO PRIOR APPLICATIONS

Under 35 U.S.C. §119, this application claims the benefit of a foreign priority application filed in Germany, serial number DE 10 2004 056 796.4, filed Nov. 24, 2004.

TECHNICAL FIELD

The present invention relates to a system for acquiring, compiling and storing measured values in a temperature and/or pressure and/or moisture-dependent process. The invention further relates to a method for monitoring a temperature and/or pressure and/or moisture-dependent process.

BACKGROUND

Laundry items, surgical tools or other medical materials must be cleaned and sterilized before they can be reused. Ordinarily this sterilization is performed by means of steam sterilization in sterilization chambers. In such a process saturated steam is fed into the sterilization chamber where it comes into direct contact with the objects to be sterilized. Maintaining specific process parameters, especially a precise temperature and constant pressure, is absolutely imperative to ensure proper sterilization. The process is monitored by means of appropriate devices.

U.S. Pat. No. 3,982,893 describes such a monitoring device. In it, sensors that continuously monitor the sterilization process can be arranged directly in the sterilization material. A digital signal is then generated from the measured values in an analog/digital converter, and is transmitted via radio to an antenna positioned inside the sterilization chamber. Via a cable that passes through the housing walls of the sterilization chamber, the antenna is connected to regulating or control devices. The apparatus thereby provides for a continuous monitoring and transmission of data. Although the arrangement of the sensors directly in the sterilization material and the transmission of the data via radio make it possible to detect the temperature inside the process material with greater precision, the passing of cables through the housing walls of the sterilization chamber is structurally costly. Furthermore, disruptions in radio contact render monitoring and verification of the sterilization process impossible.

EP 0 671 956 B1 provides for a testing unit to be positioned inside the chamber of a sterilization system. The components of this replaceable test module may comprise, for example, a temperature sensor and a pressure sensor. The testing unit is positioned at a location within the sterilizer that is near its outlet. There, the presence of air can be detected with particular accuracy using a temperature sensor. The data acquired by the testing unit are transmitted via radio to a receiver positioned outside the chamber, for real-time monitoring. When there are disruptions in radio contact, no measured data are available; thus the maintenance of process parameters can no longer be verified. As an alternative, the data may also be recorded internally, and then read out and evaluated only upon completion of the process. However in this case, problems cannot be detected in the process as it runs. A further disadvantage of this arrangement is that process data can be acquired at only a single location within the sterilizer. Furthermore, the testing unit comprises other devices for data processing and signal generation, so that the construction of a testing unit of this type is relatively costly.

SUMMARY

The system of the present invention may be used for acquiring, compiling and storing measured values and may be used in cleaning, refrigeration and heating processes, and especially in sterilization processes. The system comprises at least one sensor for acquiring measured values, which is positioned inside a closed process chamber. The walls of process chambers of this type are customarily made of metal, because of the very high or very low temperatures and high pressures that at times occur. According to the invention the device also includes a means for storing the measured values, specifically at least one data logger for storing the measured values in chronological sequence, especially at preset time intervals. For example, the data logger saves the current measured value from the allocated sensor every 10 seconds. In addition, according to the invention means are provided that allow the wireless transmission of the stored measured values at preset or settable time intervals to a receiver device positioned outside of the closed process chamber. If the stored measured values are transmitted from inside the process chamber to a receiver device positioned outside of it, then the structurally costly cable penetration is eliminated, thus substantially simplifying the construction of corresponding devices. The use of such means of transmission thus makes it possible to transmit measured data from a closed process chamber that is nearly completely enclosed by metal walls.

The system preferably comprises at least one sensor for acquiring the temperature inside the process chamber. With a temperature sensor, the presence of harmful air can be detected, for example, in a sterilization process with particular precision. If multiple sensors for acquiring the temperature are used, the process can be particularly well monitored and a temperature distribution that is essential to the process can be ensured.

An advantage of the present invention is a system that will enable an evaluation of measured data both during a process and upon its completion, and will at the same time simplify the structural implementation of devices of this type.

It is further advantageous for the system to comprise a sensor for acquiring the pressure inside the process chamber, thus improving the monitoring of the main process parameters.

Particularly preferably, each sensor is coupled to a data logger. Sensor and data logger can thereby be arranged in one common housing, or separately-connected to a data line. The data and/or process parameters from the data logger or data loggers can thus be verified during the process monitoring, preferably by means of wireless transmission at specific time intervals, and then additionally at the end of the process once the data logger has been removed from the process chamber.

Particularly precise measured values can be achieved if the at least one sensor can be positioned directly in the process material. This arrangement serves to ensure that the necessary temperatures are being reached within the process material. In the case of a sterilization process, it can thereby be ensured that the temperature is reached through condensation, and thus an adequate sterilization has taken place. The at least one sensor can also be used advantageously in a fermentation process or a refrigeration process to measure the core temperature of the process material.

It is particularly advantageous for multiple sensors and especially multiple sensor/data logger units to be positioned at different locations in the process material and/or the process chamber. Localized fluctuations in the process conditions can be detected with particular reliability with an arrangement of this type. In this it is preferable for the measured values from the various data loggers to be transmitted alternatingly to the outside. For example, the receiver device outside the process chamber can retrieve measured values from the various data loggers in sequence.

The data loggers preferably store the measured values acquired by the sensor or sensors at preset intervals, for example every 10 seconds. The retrieving receiver unit would then retrieve, for example, the six new measured values from this data logger every minute. The corresponding six measured values from another data logger could subsequently be retrieved from another location in the process chamber.

If the means for wireless transmission of the measured values from the closed process chamber comprise a radio device, a reliable transmission of data to the receiver unit positioned outside the chamber is possible. The receiver unit for the wireless transmission system is preferably designed such that it can be positioned on an outer wall of the closed process chamber. In this it is particularly advantageous for the receiver unit to be separably attached to the outer wall, for example by means of a magnetic mount or a clip device. This makes the receiver unit particularly easy to access, locate, and replace. Repair and maintenance work can also be easily performed.

One structurally simple and cost-effective design for the invention is created when a transmitting and/or receiving antenna for the radio device is formed by a coil.

One particularly advantageous further improvement on the invention provides that a system for processing and/or reading out the measured values is allocated to the device outside of the closed process chamber. This enables the process parameters to be displayed, thereby also allowing a system operator to intervene into the process. It is also possible to continue processing the measured values and to control the process by means of the measured values. Furthermore, it is possible to verify the course of the process once it has been completed, using the read-out measured values.

In a further advantageous embodiment of the invention, the receiver unit is connected via a cable connection or other data connection (for example IR transmission) to a processing and/or display unit outside of the process chamber. With this design it is especially structurally simple to provide a permanent data connection between the receiver unit and the processing and/or display unit. The individual data loggers may also be connected directly to a processing and/or display unit (without interconnection of the receiver unit) once they have been removed from the process unit, for a read out of the process parameters.

In the process specified in the invention for monitoring a temperature and/or pressure and/or moisture-dependent process, especially a sterilization process, an acquisition of measured values is accomplished by means of at least one sensor located inside a closed process chamber with metallic walls. According to the invention, the measured values are compiled and stored in at least one data logger, and during the process are transmitted at preset or settable time intervals via a wireless system to a receiver unit positioned outside the process chamber. This enables both an online monitoring and a post-process evaluation of the process parameters. Brief interruptions in transmission produce no negative effect because the measured values are stored.

The process specified in the invention further advantageously makes it possible to acquire the primary parameters using multiple sensors at various locations, and to store them in corresponding data loggers. The transmission of the data from various data loggers to the receiver unit can always be delayed, so that multiple process parameters can be reliably acquired while keeping the receiver unit structurally simple. This design makes a processing of the data prior to transmission unnecessary. The transmission of data to the receiver unit is preferably accomplished via radio waves.

One advantageous embodiment of the invention provides for the main parameters to be acquired directly within the process material. The quality of the process can thereby be monitored with particular precision.

A further advantageous improvement on the process provides for the measured values to be passed on from the receiver unit to a processing and/or display unit to allow a display of the measured values and/or for controlling the process. In this manner the process can be controlled fully automatically, or with the intervention of operating staff. It is also possible for the measured values to be verified following completion of the process.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic illustration of a system as specified in the invention with an evaluation and display unit connected in series;

FIG. 2 is a schematic, detailed view of a data logger with an internal sensor, and FIG. 3 is a schematic, detailed view of a data logger with an external sensor.

Further advantages of the invention will be described in greater detail below with reference to the exemplary embodiments.

Like reference symbols in the various drawings indicate like elements.

DETAILED DESCRIPTION

Reference is now made to the Drawings wherein like reference characters denote like or similar parts throughout the Figures.

FIG. 1 shows a schematic illustration of a system 1 of the invention, which can be used in a temperature, pressure, and/or moisture-dependent process. The process in this case takes place within a closed process chamber 2, for example a refrigerator, a furnace, a washing or rinsing machine, an autoclave or a steam sterilizer. It is also possible for the device to be used in automatic cleaning and disinfecting systems. In the present case the system 1 is comprised of multiple sensors 4, 6 to each of which a data logger 3 is allocated for the acquisition and storage of measured values, and of multiple wireless transmission units 11 and a receiver unit 10, wherein in the present case these two units are designed as antennae 10, 11. In this manner the measured values can be transmitted from the data loggers 3 to the antenna 10, which is positioned outside the process chamber 2 and acts as a receiver unit. In the present case the data loggers 3 are connected to internal sensors 4, 6 for pressure and temperature, with the term "internal" meaning that the loggers and sensors are housed within one common housing. However the use of loggers 3 with external sensors 7, as illustrated in FIG. 3, or even loggers 3 that have two sensors or a combined pressure/temperature sensor is also possible.

The measured values are compiled and stored in the data loggers 3, preferably at time intervals, for example every 10, 20 or 30 seconds of the current measured value. With this process the measured parameters can be acquired with particular precision by positioning the logger 3 directly within the process material 5. This makes the monitoring or verification of the process especially simple, since the primary parameters can be acquired and compared both at multiple locations in the process material 5 and in the process chamber 2.

According to the invention, the stored measured values are then transmitted via a wireless system to the receiver unit 10, which is positioned outside the process chamber 2, especially by means of a mounting device that is not shown in greater detail here (for example a magnetic mount or clip). With this arrangement of the receiver unit 10, costly cable penetrations through the walls of the process chamber 2 are unnecessary.

It is further provided according to the invention that the stored measured values are transmitted at preset or settable time intervals to the receiver unit 10. The measured data are thus available directly online; however any disruptions in transmission as with a real-time transmission produce no negative effect, so that the monitoring of the process can be reliably performed. Furthermore, the intermittent transmission makes it possible to transmit the measured values from different loggers 3 to a single receiver unit 10, since the transmission can be delayed, especially by retrieving the measured values that have been newly stored in the various loggers 3. However the storage of the measured values in the loggers 3 also enables a post-process verification.

The data loggers 3 along with the means for wireless transmission 11 of the measured values are arranged inside the closed process chamber 2. If the walls 8 of the process chamber 2 are made of metals, the signal transmission can take place despite the resultant Faraday shielding, for example through the rubber seals 9, as tests have surprisingly proven. To achieve this, the transmitting power of the data loggers 3 must be correspondingly strong.

The receiver unit 10 in the example shown here is connected via a permanent data connection 17 to a computer 15 for processing and display of the measured data. The processing in the computer 15 is implemented by means of appropriate software, and a printout of process protocols can be produced using the printer 16. The computer unit 15 can also be equipped with a control device for adjusting the process parameters, as is indicated by the dashed line.

FIG. 2 shows a schematic detailed view of a temperature logger 3, wherein a coil is arranged on the logger 3 as a transmitting antenna 11. The logger 3 is additionally equipped with means 12 for connecting to an interface, which enables a read-out of the data, even after the logger 3 has been removed from the process chamber 2. This permits a determination to be made regarding the quality of the finished process, even if an online monitoring becomes impossible, for example due to disruptions in transmission.

A system 1 as specified in the invention is particularly well suited for use in a sterilization process in a steam sterilizer. For the verification and monitoring of a sterilization process, at least one data logger 3 with temperature and pressure sensors 4, 6 should be used. In this case the loggers 3 must be water- and pressure-tight. In order to acquire the temperature and pressure pattern for a batch load, for example of medical instruments, it may be sufficient to position one data logger 3 with a temperature sensor 6 and a pressure sensor 4 among the items to be sterilized. Frequently, however, the acquisition of temperature values at various positions in the process chamber 2 or the process material 5 is necessary, in which case up to 12 temperature loggers and one pressure logger may be positioned in the sterilization chamber. In order also to be able to precisely determine the temperature in small hollow areas of the material being sterilized 5, which can present major problems in a sterilization process, the use of data loggers 3 with external sensors 7, as illustrated in FIG. 3, is expedient.

This arrangement is particularly well suited for temperature measurements in hollow areas into which the sensor 7 of the logger 3 can be inserted.

However, the system 1 can also be used in any other process involving temperature, pressure, and moisture parameters. An adjustment can be made to accommodate the given task by selecting the appropriate data logger 3 and by programming the measuring cycle. When the system 1 of the invention is used in refrigeration or fermentation processes it is particularly advantageous for the core temperature of the process material 5 to be acquired.

The invention is not limited to the exemplary embodiments presented. Modifications and combinations that are within the scope of the patent claims are also considered part of the invention.

A number of embodiments of the invention have been described. Nevertheless, it will be understood that various modifications may be made without departing from the spirit and scope of the invention.

What is claimed is:

1. A system for measuring processing values in a sealable process chamber defined by metallic walls and a seal, wherein the process chamber is closed and sealed after material to be processed is placed within the process chamber, said system comprising;
   a plurality of sensors, each of said sensors configured to detect a respective measured value within the sealed process chamber;
   a separate respective data logger associated with each of said sensors, said data loggers configured for disposition with the sealed process chamber to receive and store the measured values from said sensors;
   each said sensor and associated respective said data logger disposed within a separate common respective housing, wherein said plurality of housings are configured for disposition at different physically separate locations within the process chamber;
   at least one wireless transmission device configured for disposition within the sealed process chamber and alternating transmission of the stored measured values from said plurality of data loggers through the seal at predetermined time intervals during an ongoing process within the sealed process chamber; and
   a receiver unit configured for disposition outside of the process chamber to receive the transmissions from said wireless transmission device through the seal in the sealed process chamber.

2. The system of claim 1, wherein said plurality of sensors include at least one sensor for measuring the temperature inside the process chamber.

3. The system of claim 1, wherein said plurality of sensors include at least one sensor for measuring the pressure inside the process chamber.

4. The system of claim 1, wherein said plurality of sensors include at least one sensor configured for disposition directly in a process material disposed inside the closed process chamber and another of said sensors is remote from process material within the closed process chamber.

5. The system of claim 1, further comprising a separate respective wireless transmission device associated with each said data logger.

6. The system of claim 5, wherein said wireless transmission devices comprise a radio device.

7. The system of claim 6, wherein said radio devices comprise a transmitting antenna formed by a coil.

8. The system of claim 1, wherein said receiver unit is removably attachable to an outer wall of the closed process chamber.

9. The system of claim 1, further comprising a processing unit in communication with said receiver unit, and a permanent data connection between said receiver unit and said communication unit.

10. The system of claim 1, wherein the seal in the process chamber is rubber, said wireless transmission device configured to transmit through the rubber seal.

11. A method for monitoring one or more processing values selected from the group of temperature, pressure and moisture in a closed process chamber defined by metal walls and a seal, said method comprising:

disposing a plurality of separate sensors at different locations within the process chamber and measuring a respective processing value with each of the sensors during an ongoing process within the chamber;

compiling and storing the measured values from the plurality of sensors with a separate data logger disposed within the process chamber associated with each of the sensors;

each of the separate sensors and associated respective data logger disposed within a separate common housing, the plurality of housings disposed at different physically separate locations within the chamber, and at least one of the housings with respective sensor and data logger assigned for each processing value measured within the chamber; and wirelessly transmitting the compiled and stored measured values from each of the data loggers at predetermined time intervals through the seal in the process chamber to a receiver unit located outside of the process chamber.

12. The method as in claim 11, wherein the seal in the process chamber is formed at least in part by a rubber material, the measured values from the data loggers transmitted through the seal by a radio device disposed within the process chamber.

13. The method as in claim 12, comprising transmitting the measured values from the data loggers with a separate radio device associated with each respective data logger.

14. The method as in claim 11, comprising disposing at least one of the sensors within a material that is being processed within the process chamber.

15. The method as in claim 11, further including transmitting the measured values from the receiver unit to a display unit for the display of the measured values.

16. The method as in claim 11, further including transmitting the measured values from the receiver unit to a processing unit for controlling the process occurring in the closed chamber.

17. The method as in claim 11, wherein the process occurring in the closed chamber is selected from the group consisting of sterilization, refrigeration and fermentation.

* * * * *